United States Patent
Bae et al.

(10) Patent No.: US 9,896,427 B2
(45) Date of Patent: Feb. 20, 2018

(54) LIQUID CRYSTAL COMPOSITION AND LIQUID CRYSTAL DISPLAY INCLUDING THE SAME

(71) Applicant: Samsung Display Co., Ltd., Yongin-si (KR)

(72) Inventors: Ji Hong Bae, Yongin-si (KR); Keun Chan Oh, Cheonan-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/047,897

(22) Filed: Feb. 19, 2016

(65) Prior Publication Data

US 2017/0008872 A1  Jan. 12, 2017

(30) Foreign Application Priority Data

Jul. 10, 2015  (KR) .................. 10-2015-0098634

(51) Int. Cl.
| | |
|---|---|
| G02F 1/1333 | (2006.01) |
| C07D 319/06 | (2006.01) |
| C07D 309/06 | (2006.01) |
| C09K 19/34 | (2006.01) |
| C09K 19/04 | (2006.01) |
| C09K 19/12 | (2006.01) |
| C09K 19/30 | (2006.01) |

(52) U.S. Cl.
CPC ......... *C07D 319/06* (2013.01); *C07D 309/06* (2013.01); *C09K 2019/0444* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/3016* (2013.01); *C09K 2019/3019* (2013.01); *C09K 2019/3021* (2013.01); *C09K 2019/3025* (2013.01); *C09K 2019/3077* (2013.01); *C09K 2019/3422* (2013.01)

(58) Field of Classification Search
CPC .... C09K 2019/3422; C09K 2019/0444; C09K 2019/0466; C09K 2019/122; C09K 2019/123; C09K 2019/3004; C09K 2019/301; C09K 2019/3016; C09K 2019/3019; C09K 2019/3021; C09K 2019/3025; C09K 2019/3077; C07D 319/06; C07D 309/06; G02F 1/1333

USPC .............. 252/299.01, 299.6, 299.63; 428/1.1
See application file for complete search history.

(56) References Cited

U.S. PATENT DOCUMENTS

| | | | | |
|---|---|---|---|---|
| 9,416,316 | B2 * | 8/2016 | Kim ................... | C09K 19/3003 |
| 9,441,162 | B2 * | 9/2016 | Furusato ............ | C09K 19/3483 |
| 9,567,525 | B2 * | 2/2017 | Hong ................. | C09K 19/3402 |
| 2013/0207038 | A1 | 8/2013 | Haensel et al. | |
| 2014/0084210 | A1 | 3/2014 | Yanai et al. | |

FOREIGN PATENT DOCUMENTS

| | | |
|---|---|---|
| DE | 3447359 | 7/1986 |
| EP | 0135062 | 3/1985 |
| EP | 0205503 | 3/1989 |
| EP | 2883937 A1 | 6/2015 |
| JP | 2009215261 | 9/2009 |
| JP | 2014062212 | 4/2014 |
| KR | 1020140126289 A | 10/2014 |
| WO | 8603769 | 7/1986 |
| WO | 2014155531 A1 | 10/2014 |

* cited by examiner

*Primary Examiner* — Geraldina Visconti
(74) *Attorney, Agent, or Firm* — Cantor Colburn LLP

(57) ABSTRACT

A liquid crystal composition including at least one of the liquid crystal molecules represented by Chemical Formulas 1 to 3:

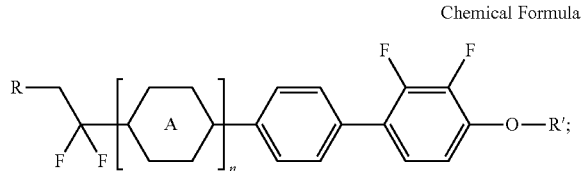

Chemical Formula 1

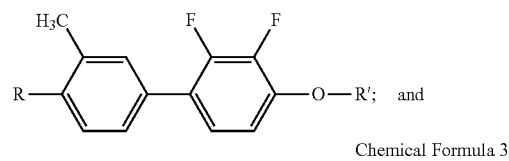

Chemical Formula 2

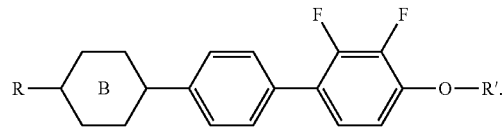

Chemical Formula 3

17 Claims, 5 Drawing Sheets

LIQUID CRYSTAL COMPOSITION AND LIQUID CRYSTAL DISPLAY INCLUDING THE SAME

This application claims priority to and the benefit of Korean Patent Application No. 10-2015-0098634, filed on Jul. 10, 2015, and all the benefits accruing therefrom under 35 U.S.C. §119, the content of which in its entirety is herein incorporated by reference.

BACKGROUND (a) Technical Field

The described technology relates generally to a liquid crystal composition and a liquid crystal display including the same.

2. Description of the Related Art

Liquid crystal displays ("LCDs") are widely used flat panel displays, which include two display panels facing each other, a liquid crystal layer interposed between two display panels, and a field generating electrode such as a pixel electrode and a common electrode positioned on at least one of the two display panels.

In an LCD, an electric field is generated in the liquid crystal layer by applying a voltage to the electric field generating electrode. In the presence of the electric field, the direction of liquid crystal molecules positioned in the liquid crystal layer may be determined and transmittance of light transmitting the liquid crystal layer may be adjusted.

In an LCD, a liquid crystal composition plays a role in adjusting transmittance of light to obtain a desired image. In particular, the liquid crystal compositions used in liquid crystal displays have various characteristics, such as a low voltage operation, a high voltage holding ratio (VHR), a wide viewing angle characteristic, a wide dynamic temperature range, high speed response, and the like.

In order for the LCD to have high-speed response characteristics, and the like, research has been conducted to improve the physical properties of the liquid crystal composition, such as rotation viscosity, refractive index, elastic coefficient, and the like.

The above information disclosed in this Background section is only to enhance the understanding of the background of the invention, and therefore it may contain information that does not form the prior art that is already known in this country to a person of ordinary skill in the art.

SUMMARY

The technology described herein provides a liquid crystal composition and a liquid crystal display including the same, having the advantages of improved transmittance and of maintaining the driving voltage.

An exemplary embodiment provides a liquid crystal composition including at least one liquid crystal molecule represented by Chemical Formulas 1 to 3 below.

Chemical Formula 1

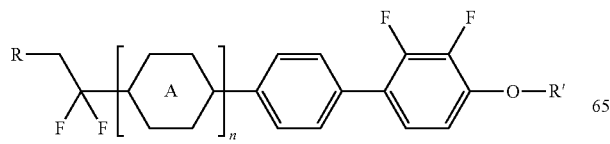

Chemical Formula 2

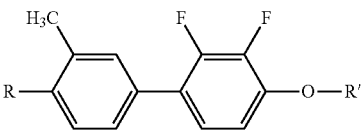

Chemical Formula 3

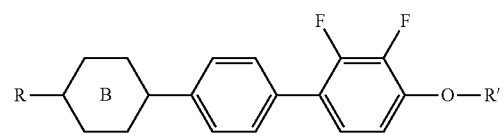

In Chemical Formulas 1 to 3 above, R and R' are each independently a hydrogen, a C1 to C5 alkyl group, a halogen group, or —CN; in Chemical Formula 1 above, n is an integer of 0 to 3, and A is of the following formulas

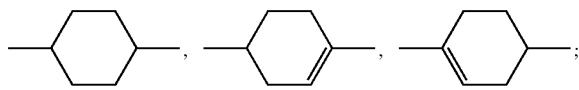

and in Chemical Formula 3 above, B is of the following formulas

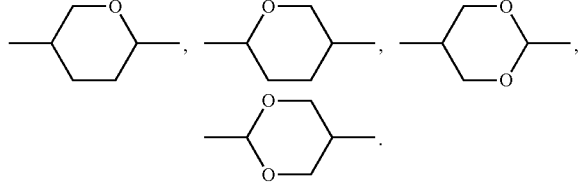

In an exemplary embodiment, the liquid crystal molecules represented by Chemical Formulas 1 to 3 include the liquid crystal molecules represented by Chemical Formula 1-1, Chemical Formula 1-2, Chemical Formula 2-1, Chemical Formula 2-2, Chemical Formula 3-1, and Chemical Formula 3-2 below.

Chemical Formula 1-1

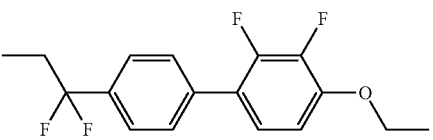

Chemical Formula 1-2

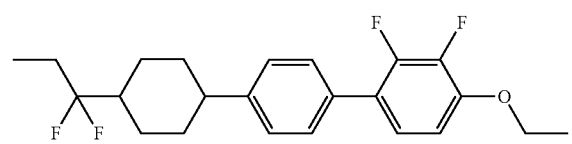

Chemical Formula 2-1

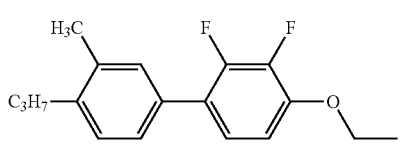

Chemical Formula 2-2

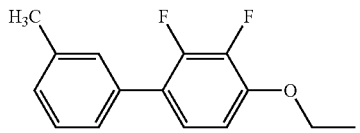

Chemical Formula 3-1

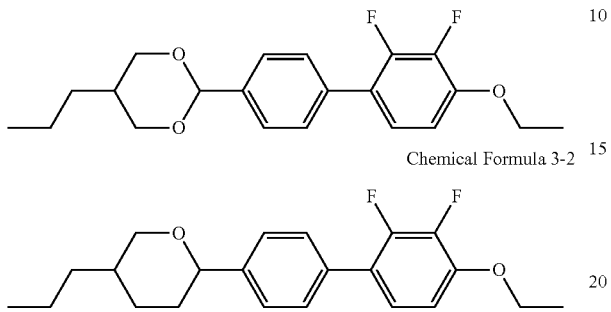

Chemical Formula 3-2

In an exemplary embodiment, the liquid crystal composition may further include at least one alkenyl-based liquid crystal molecule represented by Chemical Formulas A-1 to A-7, as below.

Chemical Formula A-1

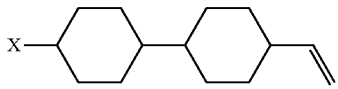

Chemical Formula A-2

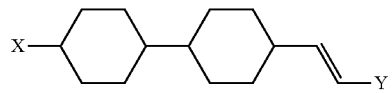

Chemical Formula A-3

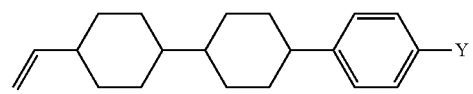

Chemical Formula A-4

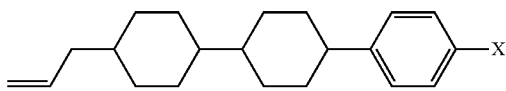

Chemical Formula A-5

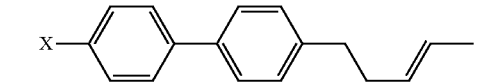

Chemical Formula A-6

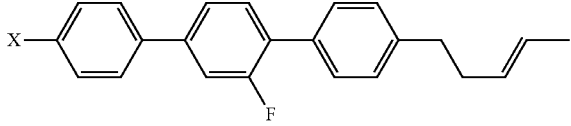

Chemical Formula A-7

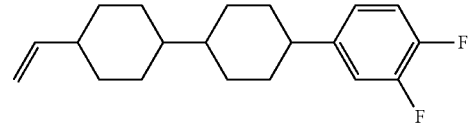

In Formulas A-1 to A-7 above, X and Y are each independently a C1 to C5 alkyl group.

In an exemplary embodiment, the liquid crystal composition may further include at least one neutral liquid crystal molecule represented by Chemical Formulas N-1 to N-5 below.

Chemical Formula N-1

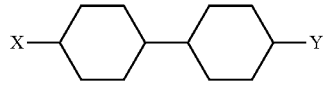

Chemical Formula N-2

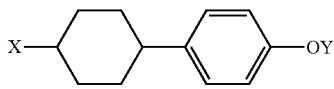

Chemical Formula N-3

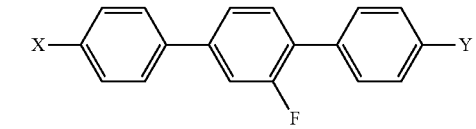

Chemical Formula N-4

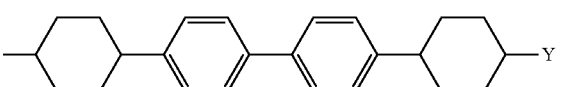

Chemical Formula N-5

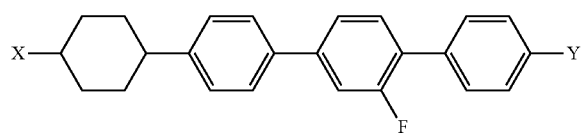

In Chemical Formulas N-1 to N-5 above, X and Y are each independently a C1 to C5 alkyl group.

In an exemplary embodiment, the liquid crystal composition may further include at least one polar liquid crystal molecule represented by Chemical Formulas P-1 to P-12, as below.

Chemical Formula P-1

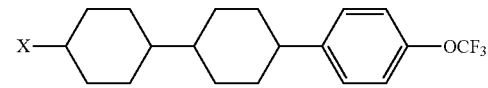

Chemical Formula P-2

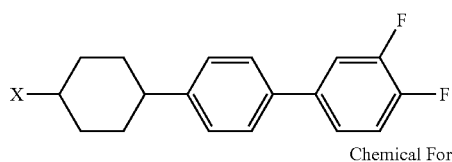

Chemical Formula P-3

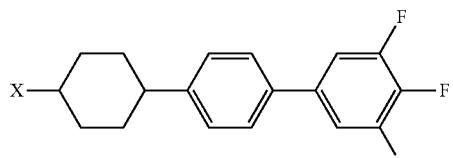

-continued

Chemical Formula P-4

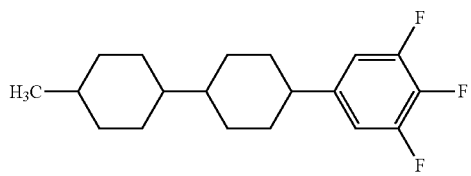

Chemical Formula P-5

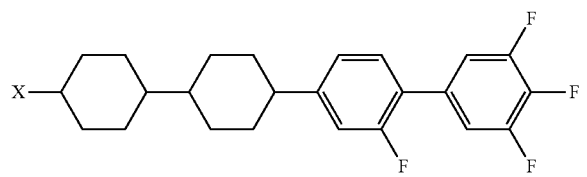

Chemical Formula P-6

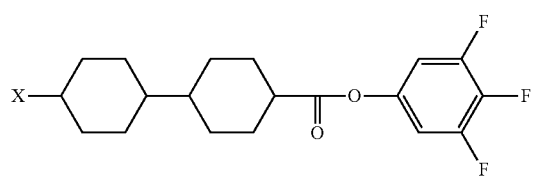

Chemical Formula P-7

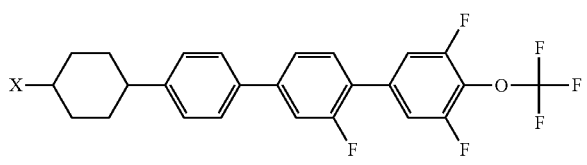

Chemical Formula P-8

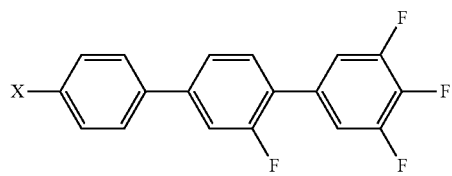

Chemical Formula P-9

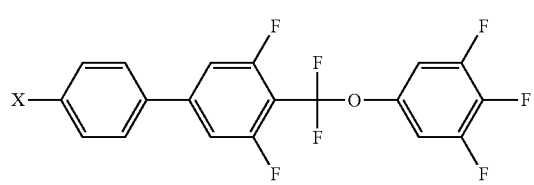

Chemical Formula P-10

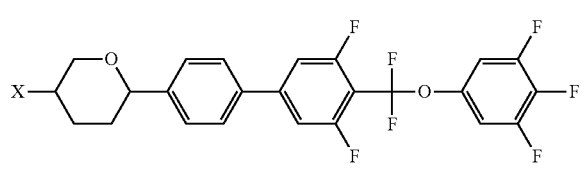

Chemical Formula P-11

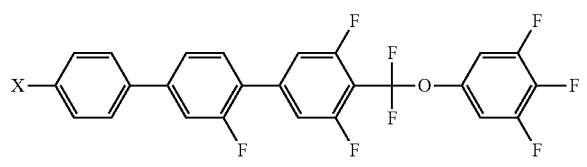

Chemical Formula P-12

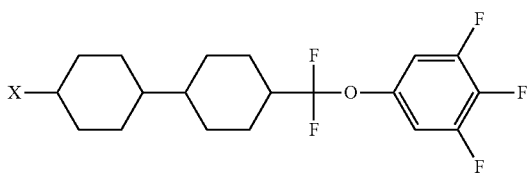

In Chemical Formulas P-1 to P-12 above, X and Y are each independently a C1 to C5 alkyl group.

In an exemplary embodiment, the liquid crystal composition includes about 1 weight percent (wt %) to about 20 wt % of at least one of the liquid crystal molecules represented by Chemical Formula 1-1, Chemical Formula 1-2, Chemical Formula 2-1, Chemical Formula 2-2, Chemical Formula 3-1, and Chemical Formula 3-2, based on the entire weight of the composition.

Another exemplary embodiment provides a liquid crystal display including: a first substrate, a first electrode and a second electrode positioned on the first substrate, with an insulating layer interposed between the first electrode and the second electrode, a second substrate facing the first substrate; and a liquid crystal layer positioned between the first substrate and the second substrate, wherein the liquid crystal layer includes at least one liquid crystal molecule represented by Chemical Formulas 1 to 3 below.

Chemical Formula 1

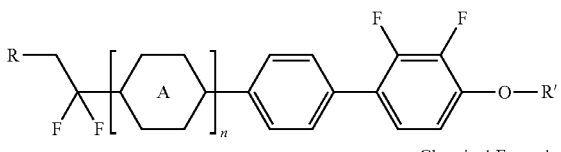

Chemical Formula 2

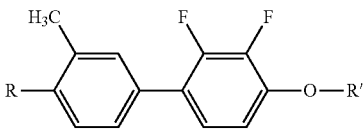

Chemical Formula 3

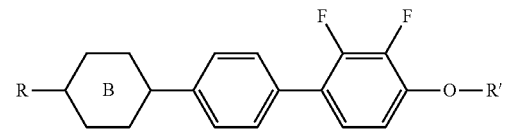

In Chemical Formulas 1 to 3 above, R and R' are each independently a hydrogen, a C1 to C5 alkyl group, a halogen group, or —N; in Chemical Formula 1 above, n is an integer from 0 to 3, and A is of the following formulas and in Chemical Formula 3 above, B is of the following formulas

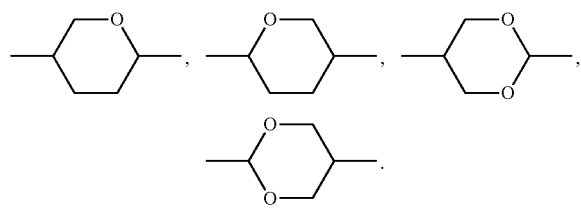

In an exemplary embodiment, the liquid crystal molecules represented by Chemical Formulas 1 to 3 include the liquid crystal molecules represented by Chemical Formula 1-1, Chemical Formula 1-2, Chemical Formula 2-1, Chemical Formula 2-2, Chemical Formula 3-1, and Chemical Formula 3-2 below.

Chemical Formula 1-1

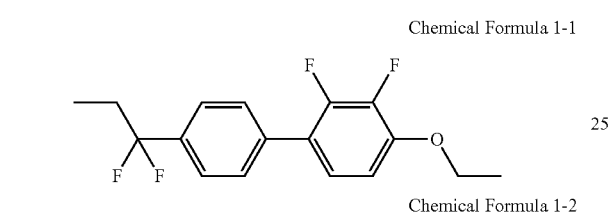

Chemical Formula 1-2

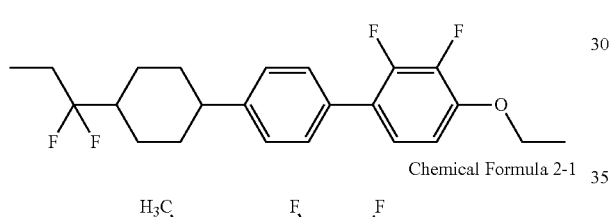

Chemical Formula 2-1

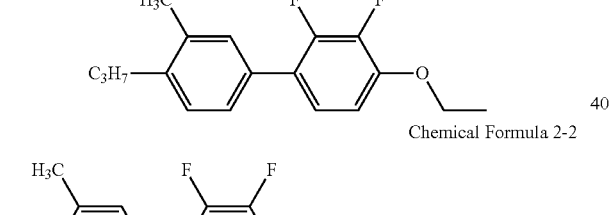

Chemical Formula 2-2

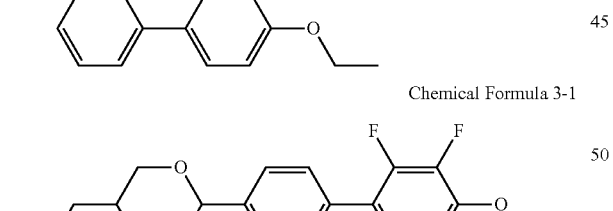

Chemical Formula 3-1

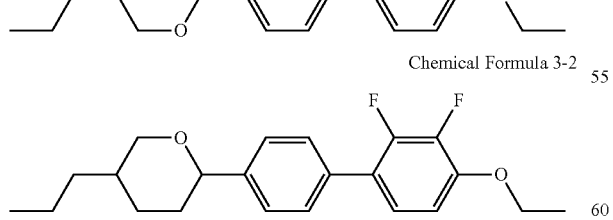

Chemical Formula 3-2

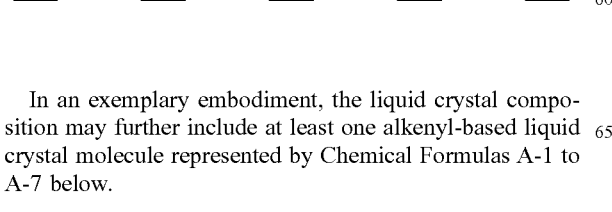

In an exemplary embodiment, the liquid crystal composition may further include at least one alkenyl-based liquid crystal molecule represented by Chemical Formulas A-1 to A-7 below.

Chemical Formula A-1

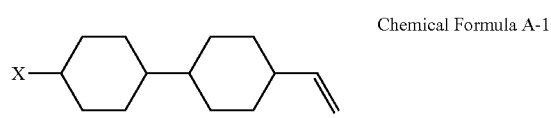

Chemical Formula A-2

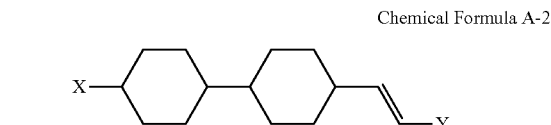

Chemical Formula A-3

Chemical Formula A-4

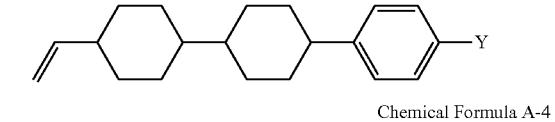

Chemical Formula A-5

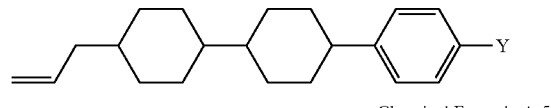

Chemical Formula A-6

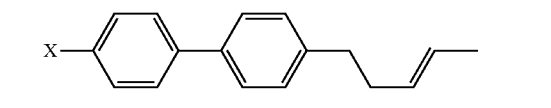

Chemical Formula A-7

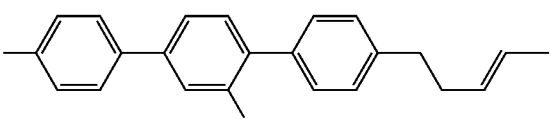

In Formulas A-1 to A-7 above, X and Y are each independently a C1 to C5 alkyl group.

In an exemplary embodiment, the liquid crystal composition may further include at least one neutral liquid crystal molecule represented by Chemical Formulas N-1 to N-5, as below.

Chemical Formula N-1

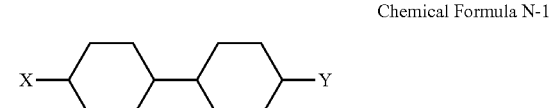

Chemical Formula N-2

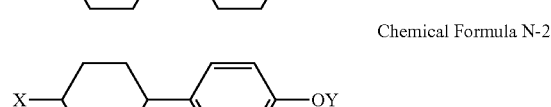

Chemical Formula N-3

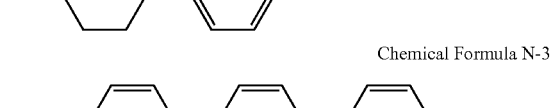

-continued

Chemical Formula N-4

Chemical Formula N-5

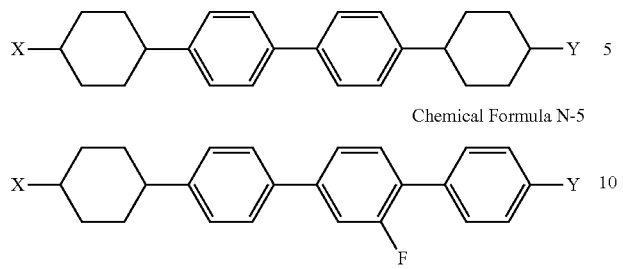

In Chemical Formulas N-1 to N-5 above, X and Y are each independently a C1 to C5 alkyl group.

In an exemplary embodiment, the liquid crystal composition may further include at least one polar liquid crystal molecule represented by Chemical Formulas P-1 to P-12, as below.

Chemical Formula P-1

Chemical Formula P-2

Chemical Formula P-3

Chemical Formula P-4

Chemical Formula P-5

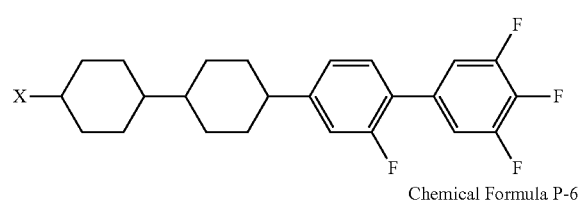

Chemical Formula P-6

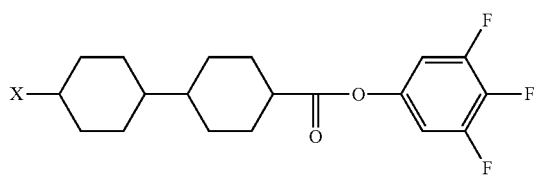

-continued

Chemical Formula P-7

Chemical Formula P-8

Chemical Formula P-9

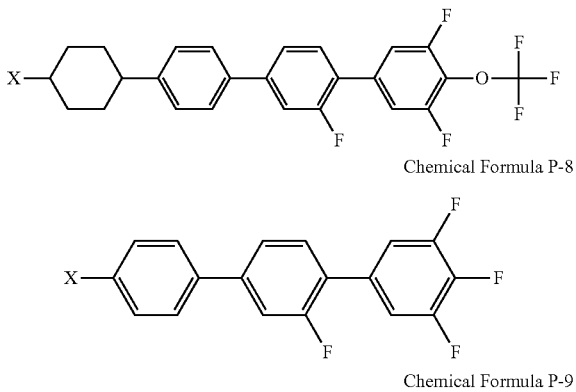

Chemical Formula P-10

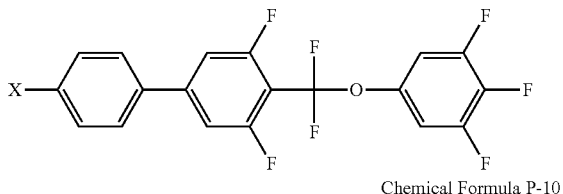

Chemical Formula P-11

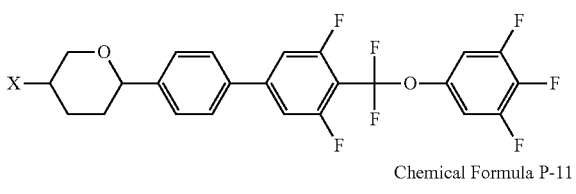

Chemical Formula P-12

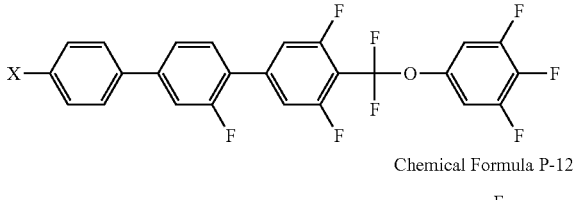

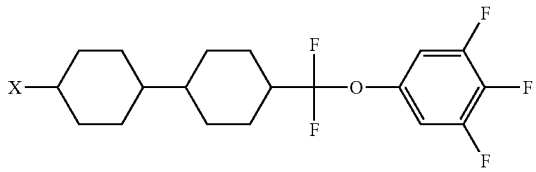

In Chemical Formulas P-1 to P-12 above, X and Y are each independently a C1 to C5 alkyl group.

In an exemplary embodiment, the liquid crystal layer includes about 1 wt % to about 20 wt % of at least one liquid crystal molecule represented by Chemical Formula 1-1, Chemical Formula 1-2, Chemical Formula 2-1, Chemical Formula 2-2, Chemical Formula 3-1, and Chemical Formula 3-2, based on the entire weight of the liquid crystal layer.

In an exemplary embodiment, the liquid crystal molecules included in the liquid crystal layer are tilted in a direction parallel to branch electrodes when an electric field is not applied to the liquid crystal layer.

In an exemplary embodiment, the liquid crystal molecules are tilted in a direction horizontal to an electric field when the electric field is applied to the liquid crystal layer.

According to an exemplary embodiment, the liquid crystal display is capable of improving transmittance and of maintaining driving voltage by using the liquid crystal composition described herein having a novel structure for the liquid crystal molecules.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
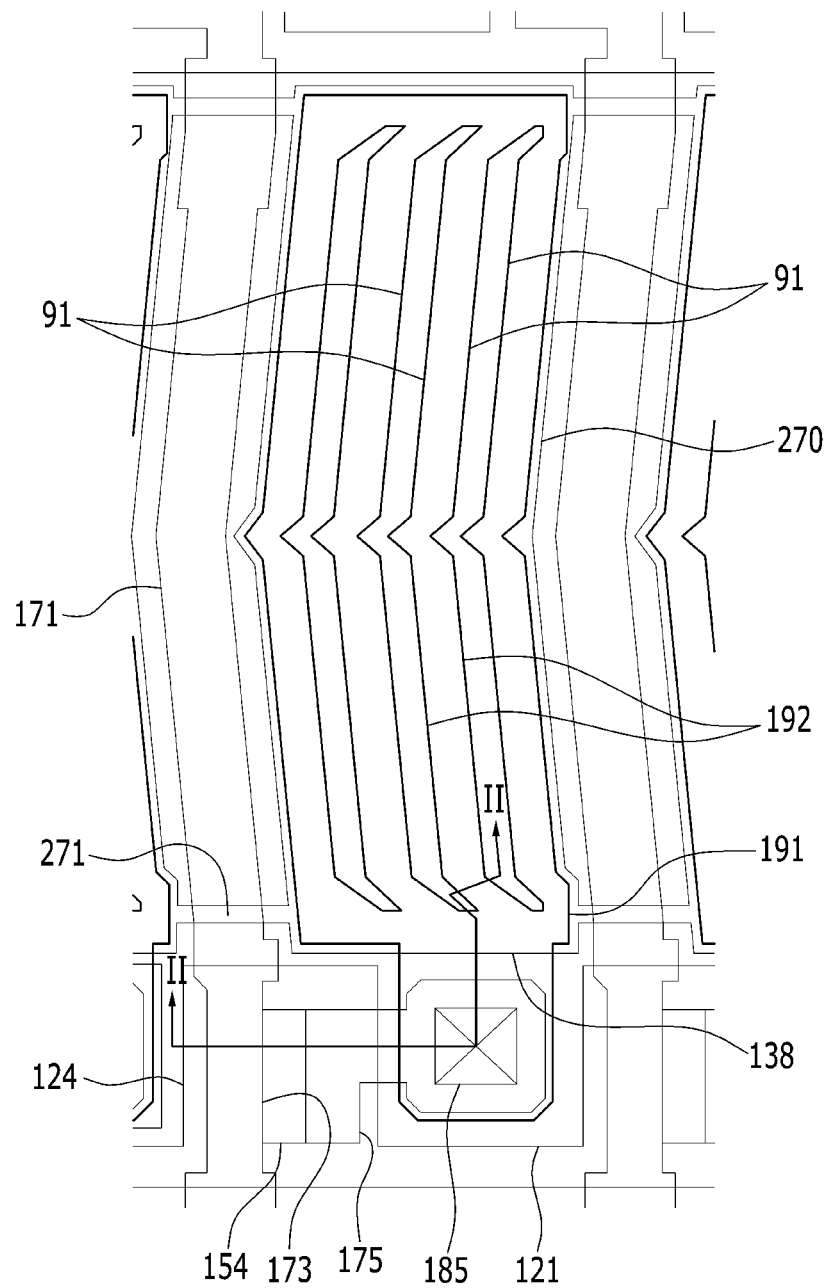
FIG. 1 is a top plan view of an exemplary embodiment of a liquid crystal display.

Hereinafter, exemplary embodiments will be described in detail with reference to the accompanying drawings in which various embodiments are shown. However, the present invention is not limited to the exemplary embodiments which are described herein, and may be modified in various different ways. Rather, the exemplary embodiments to be described below are provided so that the idea of the present invention can be sufficiently transferred to those skilled in the art to which the present invention pertains.

In the drawings, thicknesses of layers and regions are exaggerated for clarity. In addition, in the case it is stated that a layer is present 'on' another layer or a substrate, the layer may be directly formed on the other layer or the substrate or have another layer interposed therebetween. Portions denoted by like reference numerals mean like elements throughout the specification.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In an exemplary embodiment, a liquid crystal composition includes at least one of the liquid crystal molecules represented by Chemical Formulas 1 to 3, as below.

Chemical Formula 1

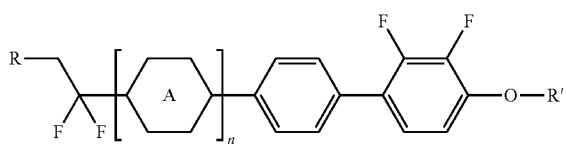

-continued

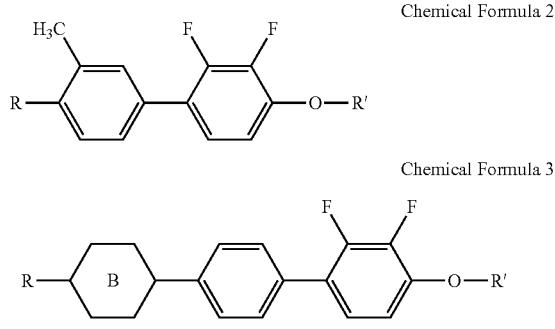
Chemical Formula 2

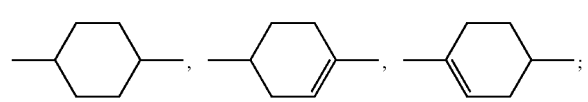
Chemical Formula 3

In Chemical Formula 1 above, n is an integer from 0 to 3 and A is of the following formulas

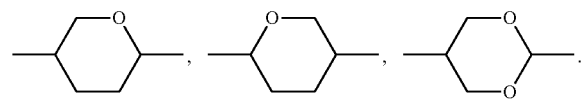

while in Chemical Formula 3 above, B is of the following formulas

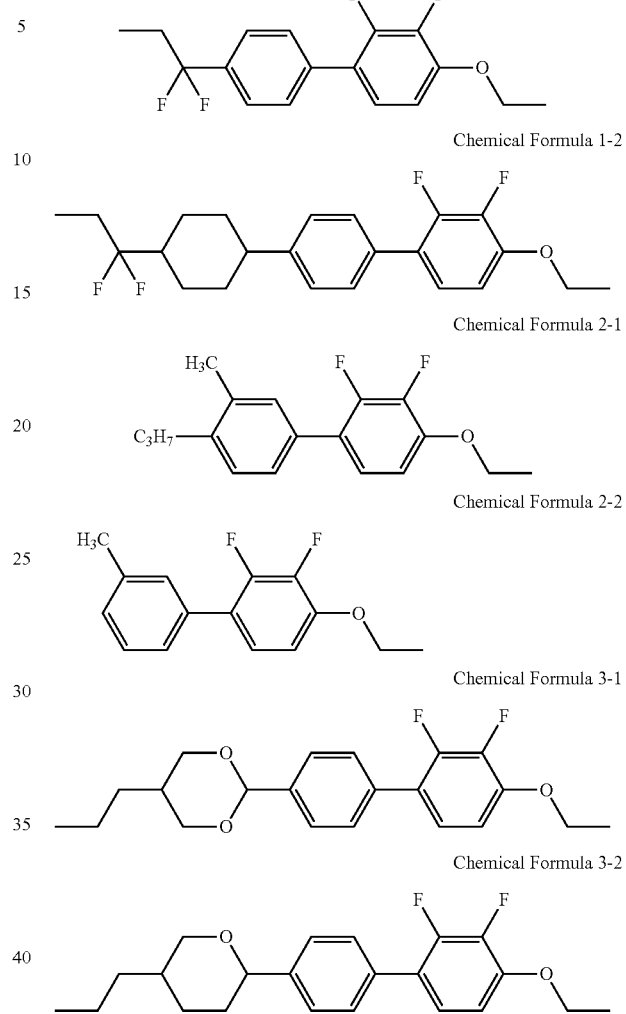

In addition, in Chemical Formulas 1 to 3 above, R and R' are each independently a hydrogen, a C1 to C5 alkyl group, a halogen group, or —CN As illustrated above, Chemical Formula 1 includes a difluorine group, Chemical Formula 2 includes a biphenyl having a methyl group in a meta-position on one of the phenyl groups, and Chemical Formula 3 includes a pyran group or a 1,3-dioxane. More particularly, the liquid crystal molecules represented by Chemical Formulas 1 to 3 have a negative dielectric anisotropy.

At least one of the liquid crystal molecules represented by Chemical Formulas 1 to 3 may be present in the liquid crystal composition in an amount of about 1 wt % to 20 wt %, based on the weight of the entire liquid crystal composition. Specifically, the liquid crystal molecules are present in an amount of about 15 wt %.

The liquid crystal molecules represented by Chemical Formulas 1 to 3 includes the liquid crystal molecules represented by Chemical Formula 1-1 and Chemical Formula 1-2, Chemical Formula 2-1 and Chemical Formula 2-2, Chemical Formula 3-1 and Chemical Formula 3-2, as shown below. Specifically, the liquid crystal molecules represented by Chemical Formula 1 includes the liquid crystal molecule represented by Chemical Formulas 1-1 and 1-2 below, the liquid crystal molecule represented by Chemical Formula 2 includes the liquid crystal molecule represented by Chemical Formulas 2-1 and 2-2 below, and the liquid crystal molecule represented by Chemical Formula 3 includes the liquid crystal molecule represented by Chemical Formulas 3-1 and 3-2 below, respectively.

Table 1 below shows physical properties of the liquid crystal molecules represented by Chemical Formulas 1-1 and 1-2, the liquid crystal molecules represented by Chemical Formulas 2-1 and 2-2, and the liquid crystal molecules represented by 3-1 and 3-2.

TABLE 1

| Compound | Dipole Moment | Total Energy (*Kcal/mol) | Refractive anisotropy (n) | Dielectric anisotropy ($\epsilon$) |
|---|---|---|---|---|
| Chemical Formula 1-1 | 3.49 | 23.22 | 0.16 | −8.5 |
| Chemical Formula 1-2 | 3.48 | 30.71 | 0.18 | −8.4 |
| Chemical Formula 2-1 | 3.50 | 22.15 | 0.15 | −8.2 |
| Chemical Formula 2-2 | 3.40 | 18.37 | 0.15 | −8.3 |
| Chemical Formula 3-1 | 5.35 | 40.88 | 0.17 | −8.0 |
| Chemical Formula 3-2 | 3.82 | 31.13 | 0.17 | −7.9 |

*Kcal/mol = kilocalories per mole.

In an exemplary embodiment, the liquid crystal composition may further include at least one of the alkenyl-based liquid crystal molecules represented by Chemical Formulas A-1 to A-7, as shown below.

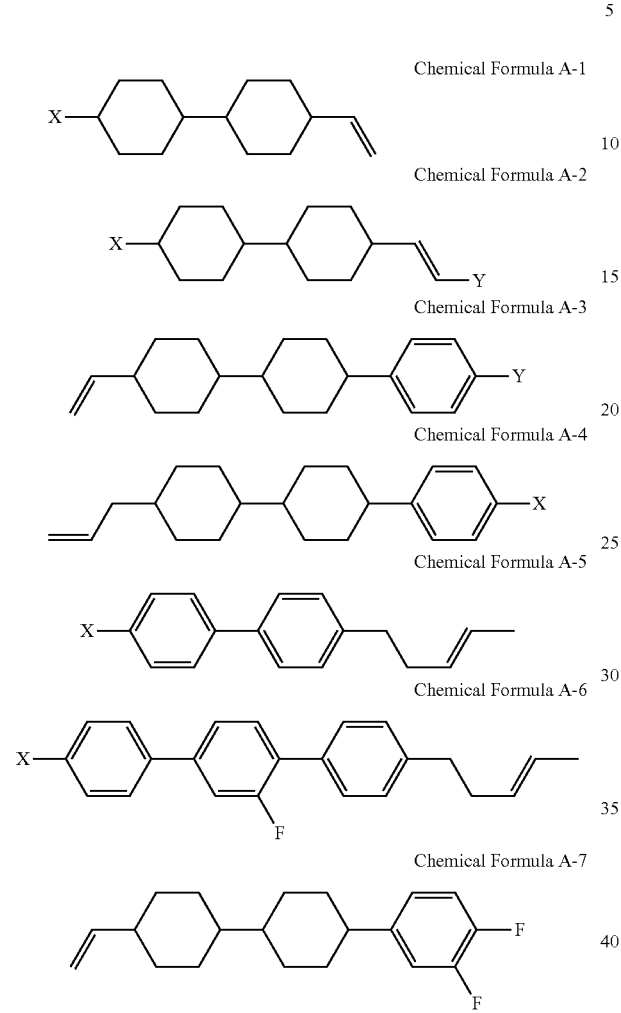

In Chemical Formulas A-1 to A-7 above, X and Y are each independently a C1 to C5 alkyl group.

The alkenyl-based liquid crystal molecules represented by Chemical Formulas A-1 to A-7 above may be low viscosity neutral liquid crystals and may exhibit high speed response characteristics due to a relatively low rotational viscosity as compared to liquid crystal molecules with other functional groups.

However, when the liquid crystal composition contains too much of the alkenyl-based liquid crystal molecules represented by Chemical Formulas A-1 to A-7, a liquid crystal display according to an exemplary embodiment may generate defects due to the strong reactivity of the carbon-carbon double bond. The liquid crystal composition may include up to about [55] wt % of the alkenyl-based liquid crystal molecules, based on the entire weight of the composition.

In an exemplary embodiment, the liquid crystal composition may further include at least one of the neutral liquid crystal molecules represented by Chemical Formulas N-1 to N-7, as shown below.

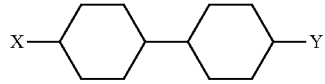

Chemical Formula N-1

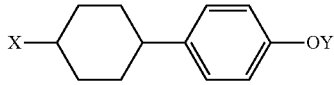

Chemical Formula N-2

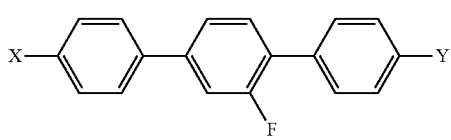

Chemical Formula N-3

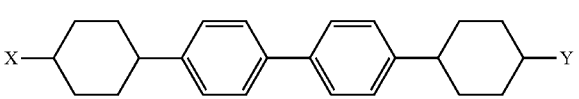

Chemical Formula N-4

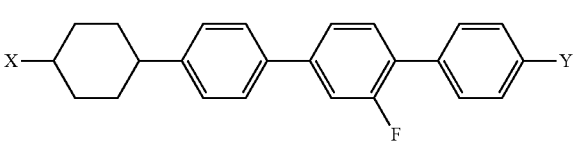

Chemical Formula N-5

In Chemical Formulas N-1 to N-7 above, X and Y are each independently a C1 to C5 alkyl group.

The neutral liquid crystal molecules represented by Chemical Formulas N-1 to N-5 above may have a high refractive anisotropy characteristic and a low rotational viscosity characteristic as compared to other liquid crystal molecules.

The liquid crystal composition may further include at least one of the polar liquid crystal molecules represented by Chemical Formulas P-1 to P-12, as below.

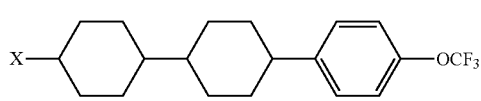

Chemical Formula P-1

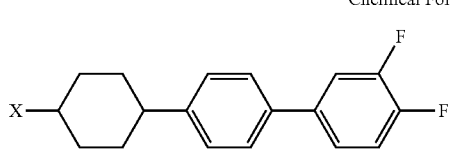

Chemical Formula P-2

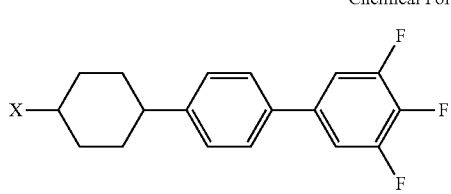

Chemical Formula P-3

-continued

Chemical Formula P-4

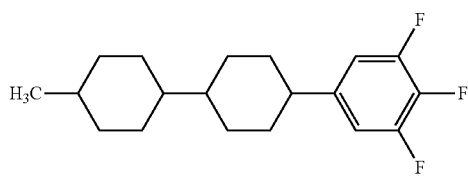

Chemical Formula P-5

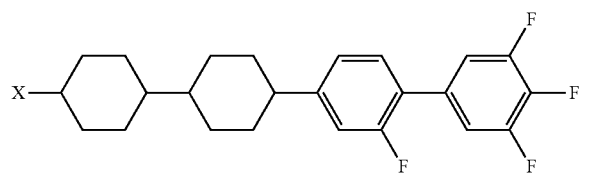

Chemical Formula P-6

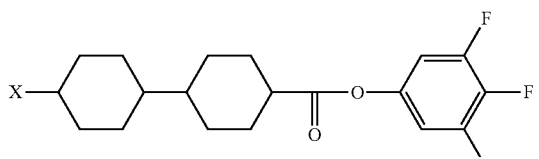

Chemical Formula P-7

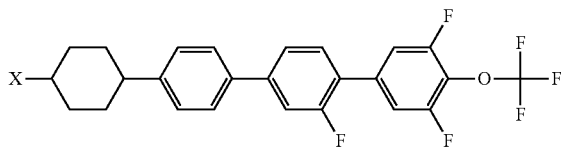

Chemical Formula P-8

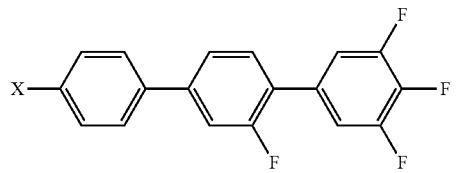

Chemical Formula P-9

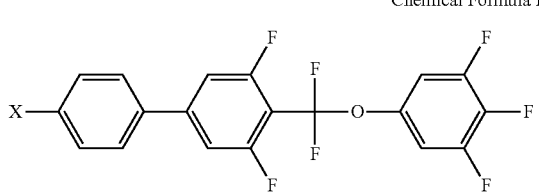

Chemical Formula P-10

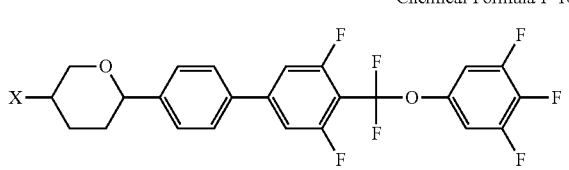

Chemical Formula P-11

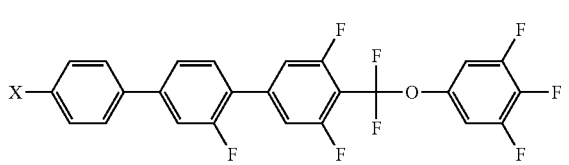

-continued

Chemical Formula P-12

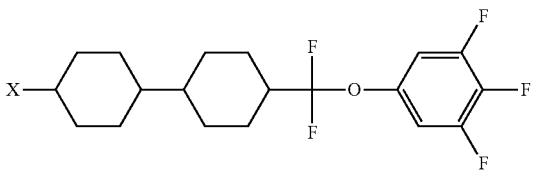

In Chemical Formulas P-1 to P-12 above, X and Y are each independently a C1 to C5 alkyl group.

Hereinafter, a liquid crystal display manufactured using the liquid crystal composition described above will be described.

Figure 2:
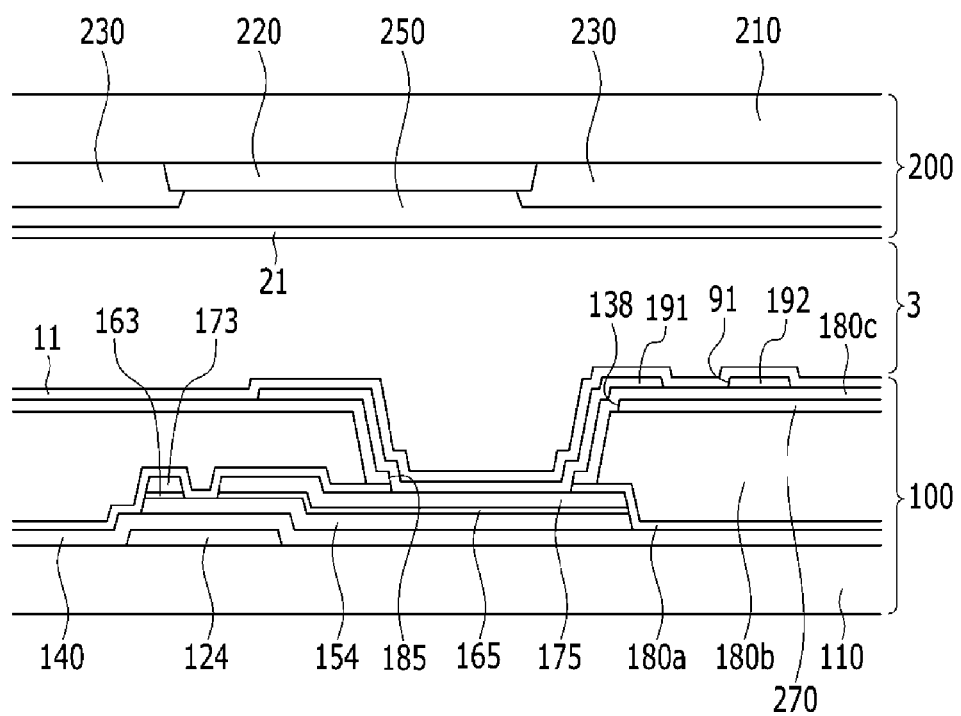
FIG. 2 is a cross-sectional view taken along line II-II of FIG. 1.

FIG. 1 is a top plan view of an exemplary embodiment of the liquid crystal display according to an exemplary embodiment. FIG. 2 is a cross-sectional view taken along line II-II of FIG. 1.

Referring to FIGS. 1 and 2, the exemplary liquid crystal display includes a lower display panel 100 and an upper display panel 200, and a liquid crystal layer 3 interposed therebetween, wherein the lower display panel and the upper display panel face each other.

First, the lower display panel 100 will be described.

A gate conductor including a gate line 121 is formed on a first substrate 110 formed of transparent glass, plastic, or the like.

The gate line 121 may include a wide end portion (not shown) for allowing a connection with a gate electrode 124 and other layers or external driving circuits. The gate line 121 may be formed of an aluminum-based metal such as aluminum (Al), aluminum alloy, and the like, a silver-based metal such as silver (Ag), silver alloy, and the like, a copper-based metal such as copper (Cu), copper alloy, and the like, a molybdenum-based metal such as molybdenum (Mo), molybdenum alloy, and the like, chromium (Cr), tantalum (Ta), titanium (Ti), and the like. The gate line 121 may have a multilayer structure including at least two conductive layers having different physical properties.

A gate insulating layer 140 formed of silicon nitride (SiNx), silicon oxide (SiOx), or the like, is formed on the gate line 121. The gate insulating layer 140 may have a multilayer structure including at least two insulating layers having different physical properties.

A semiconductor layer 154 formed of amorphous silicon, polysilicon, or the like, is formed on the gate insulating layer 140. The semiconductor layer 154 may be formed of an oxide semiconductor.

Ohmic contacts 163 and 165 are formed on the semiconductor layer 154. The ohmic contacts 163 and 165 may be formed of n+ hydrogenated amorphous silicon materials in which n-type impurities such as phosphorus are doped at a high concentration or may be formed of silicide. The ohmic contacts 163 and 165 may be disposed in pairs on the semiconductor layer 154. When the semiconductor layer 154 is an oxide semiconductor, the ohmic contacts 163 and 165 may be omitted.

A data line 171 including the source electrode 173 and a data conductor including a drain electrode 175 are formed on the ohmic contacts 163 and 165 and the gate insulating layer 140.

The data line 171 includes a wide end portion (not shown) for allowing a connection with other layers or external driving circuits (not shown). The data line 171 transmits a data signal, is mainly extended in a vertical direction, and intersects the gate line 121.

The data line 171 may have a curved portion having a bent shape in order to obtain maximum transmittance of the liquid crystal display, and the curved portion may be bent at a middle region of the pixel area to form a V shape.

The source electrode 173 is a portion of the data line 171, and is disposed on the same line as the data line 171. The drain electrode 175 is extended so as to be parallel to the source electrode 173. Therefore, the drain electrode 175 is parallel to a portion of the data line 171.

The gate electrode 124, the source electrode 173, and the drain electrode 175 together with the semiconductor layer 154 form one thin film transistor (TFT). A channel of the thin film transistor is formed on the semiconductor layer 154 between the source electrode 173 and the drain electrode 175.

In an exemplary embodiment, the liquid crystal display may include the source electrode 173 positioned on the same line as the data line 171, and the drain electrode 175 extending parallel to the data line 171, to widen a width of the thin film transistor without widening an area occupied by the data conductor. Accordingly, an aperture ratio of the liquid crystal display may be increased.

The data line 171 and the drain electrode 175 are formed of refractory metals such as molybdenum, chromium, tantalum, titanium, and the like, or alloys thereof. The data line 171 and the drain electrode 175 may have a multilayer structure including a refractory metal layer (not shown) and a low-resistance conductive layer (not shown). Examples of the multilayer structure may include a bi-layer having a chromium or molybdenum (alloy) lower layer and an aluminum (alloy) upper layer, and a triple-layer having a molybdenum (alloy) lower layer, an aluminum (alloy) intermediate layer and a molybdenum (alloy) upper layer.

A first passivation layer 180a is disposed on portions in which the data conductors 171, 173 and 175, the gate insulating layer 140, and the semiconductor layer 154 are exposed. The first passivation layer 180a may be formed of organic insulating materials, inorganic insulating materials, or the like.

A second passivation layer 180b is formed on the first passivation layer 180a. The second passivation layer 180b may be formed of an organic insulating material.

The second passivation layer 180b may be a color filter. When the second passivation layer 180b is the color filter, the second passivation layer 180b may uniquely show one primary color. Examples of primary colors may include three primary colors such as red, green, and blue, or yellow, cyan, and magenta. Although not shown, the color filter may further include a color filter expressing a mix of the primary colors, or white in addition to the primary color. In the case in which the second passivation layer 180b is the color filter, the upper display panel 200 (described below) may omit the color filter 230. Unlike the present exemplary embodiment, the second passivation layer 180b may be formed of organic insulating materials, and a color filter (not shown) may be positioned between the first passivation layer 180a and the second passivation layer 180b.

A common electrode 270 is positioned on the second passivation layer 180b. The common electrode 270 has a planar shape and may be formed in integrated plate shape on a front surface of the substrate 110. The common electrode 270 has an opening 138 disposed in a region corresponding to the periphery of the drain electrode 175. The opening 138 may be extended in a direction parallel to the gate line 121, and may be formed in an isolated form even in a portion overlapping the data line 171. That is, in the present exemplary embodiment, the common electrode 270 may have an integrated plate shape which is connected without being split into portions corresponding to unit pixels. Here, the common electrode portions 270 of respective neighboring pixels in a direction of the gate line 121 may be connected through a connection part 271.

The common electrodes 270 positioned on adjacent pixels may be connected to each other to receive a common voltage having a predetermined size supplied from a source outside of the display area.

An insulating layer 180c is positioned on the common electrode 270. The insulating layer 180c may be formed of organic insulating materials, inorganic insulating materials, or the like.

A pixel electrode 191 is positioned on the insulating layer 180c. The pixel electrode 191 includes curved edges nearly parallel to the curved portion of the data line 171. The pixel electrode 191 has a plurality of cutouts 91, and includes a plurality of branch electrodes 192 positioned between neighboring cutouts 91. In a plane view, the plurality of branch electrodes 192 overlaps the common electrode 270.

The pixel electrode 191 is a first field generating electrode or a first electrode, and the common electrode 270 is a second field generating electrode or a second electrode. The pixel electrode 191 and the common electrode 270 may form a fringe field.

A contact hole 185 exposing the drain electrode 175 is formed in the first passivation layer 180a, the second passivation layer 180b, and the insulating layer 180c. The pixel electrode 191 is electrically connected to the drain electrode 175 through the contact hole 185 to thereby receive a voltage applied from the drain electrode 175.

A first alignment layer 11 is formed on the pixel electrode 191 and the insulating layer 180c. The first alignment layer 11 may be a horizontal alignment layer, and may be rubbed in a predetermined direction. However, the first alignment layer 11 is not limited to the rubbing alignment layer, but may also be a photo-alignment layer.

The upper display panel 200 will now be described.

A light blocking member 220 is formed on a second substrate 210 made of transparent glass, plastic, or the like. The light blocking member 220 is also called a black matrix, and prevents light leakage.

A plurality of color filters 230 are also formed on the second substrate 210. When the second passivation layer 180b of the lower display panel 100 is a color filter, or when the color filter is formed on the lower display panel 100, the color filter 230 of the upper display panel 200 may be omitted. In addition, the light blocking member 220 of the upper display panel 200 may also be formed on the lower display panel 100.

An overcoat 250 is formed on the color filter 230 and the light blocking member 220. The overcoat 250 may be formed of an (organic) insulating material, and prevents the color filter 230 from being exposed, and provides a flat surface. The overcoat 250 is optional and may be omitted.

A second alignment layer 21 is formed on the overcoat 250. The second alignment layer 21 may be formed of the same materials as the first alignment layer 11.

The liquid crystal layer 3 is interposed between the lower display panel 100 and the upper display panel 200. In an exemplary embodiment, the liquid crystal layer 3 includes at least one of the liquid crystal molecules of Chemical Formulas 1 to 3. The liquid crystal molecules have a novel structure, such as Chemical Formula 1 including a difluorine group, Chemical Formula 2 including a biphenyl group having a methyl group in a meta position on one of the phenyl rings, and Chemical Formula 3 having a pyran or 1,3-dioxane group. The above specific description regarding the liquid crystal composition may be applied thereto.

Figure 3:
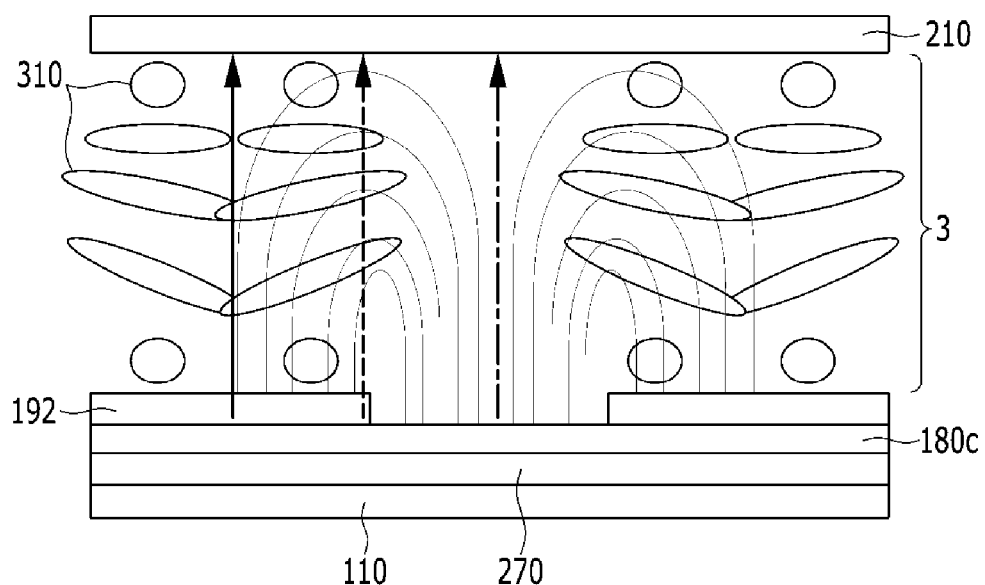
FIG. 3 is a cross-sectional view schematically showing the alignment of liquid crystal molecules according to whether or not an electric field is applied in the exemplary embodiment of a liquid crystal display.

FIG. 3 is a cross-sectional view schematically showing alignment of liquid crystal molecules according to whether or not an electric field is applied to the exemplary liquid crystal display.

Referring to FIG. 2 and FIG. 3, an exemplary embodiment of a first alignment layer 11 and a second alignment layer 21 may be rubbed in a direction parallel to the plurality of branch electrodes 192.

The liquid crystal molecules 310 of the liquid crystal layer 3 may be aligned so that a direction of a major axis thereof is parallel to the display panels 100 and 200. In particular, the major axis of the liquid crystal molecules 310 may be extended in a direction parallel to the plurality of branch electrodes 192 in an off state in which an electric field is not applied. In other words, the liquid crystal molecules 310 are tilted in a direction in which the branch electrodes 192 are extended when an electric field is not applied to the liquid crystal layer.

Referring to FIG. 1 to FIG. 3, the exemplary liquid crystal display is a plane to line switching mode liquid crystal display in which an electric field is formed in the liquid crystal layer 3 by a planar field generating electrode and a linear field generating electrode, particularly in the case where the insulating layer is interposed therebetween.

Referring back to FIGS. 1 and 2, the pixel electrode 191 receives a data voltage from the drain electrode 175, and the common electrode 270 receives a predetermined amount of common voltage from a common voltage applying part disposed on the outside of the display area.

The pixel electrode 191 and the common electrode 270, which are field generating electrodes, may generate an electric field, such that the liquid crystal molecules 310 of the liquid crystal layer 3 positioned on two field generating electrodes 191 and 270, may be tilted in a direction vertical to the direction of the electric field or may rotate in a direction parallel to the direction of an electric field. When an electric field is applied to the liquid crystal layer 3, the liquid crystal molecules 310 may be tilted in a direction horizontal to the electric field. Polarization of light passing the liquid crystal layer is changed depending upon the rotation direction of the liquid crystal molecules as described above.

As described above, two field generating electrodes 191 and 270 may be formed on one display panel 100 to increase transmittance of the liquid crystal display and implement a photo-viewing angle.

In an exemplary embodiment of the liquid crystal display, the common electrode 270 has a planar flat shape, and the pixel electrode 191 has the plurality of branch electrodes. However, in an alternative exemplary embodiment, the pixel electrode 191 may have the planar flat shape, and the common electrode 270 may have the plurality of branch electrodes.

The present invention is applicable to all other cases in which two field generating electrodes overlap on the first substrate 110 with the insulating layer interposed therebetween, the first field generating electrode formed below the insulating layer has the planar flat shape, and the second field generating electrode formed on the insulating layer has the plurality of branch electrodes.

The display panels 100 and 200 may have polarizers (not shown) provided on outer surfaces thereof, wherein transmission axes of the polarizers are orthogonal to each other, and one of the transmission axes is preferably parallel to the gate line 121. One of two polarizers may be omitted in a reflective liquid crystal display.

Hereinafter, examples of a liquid crystal composition and physical properties thereof are described.

COMPARATIVE EXAMPLE

A comparative a liquid crystal composition (Comparative Example) is shown below in Table 2.

TABLE 2

| Liquid crystal compound | Content (wt %) |
|---|---|
| Chemical Formula A-1 | 34 |
| Chemical Formula A-2 | 7 |
| Chemical Formula A-3 | 10.5 |
| Chemical Formula N-3 | 16.5 |
| Chemical Formula P-1 | 8 |
| Chemical Formula P-5 | 3.5 |
| Chemical Formula P-9 | 15 |
| Chemical Formula P-12 | 5.5 |

In Table 2 above, the liquid crystal compound of the Comparative Example includes compounds represented by Chemical Formulas A-1, A-2, A-3, N-3, P-1, P-5, P-9, and P-12. Specifically, all of the liquid crystal molecules included in the Comparative Example are compounds having a positive dielectric anisotropy ($\Delta\epsilon$).

The physical properties of the Comparative Example were as follows: the nematic-isotropic phase transition temperature (Tni) was 79 degrees Celsius (° C.), the refractive index ($\Delta$n) was 0.110, the dielectric anisotropy ($\Delta\epsilon$) was 5.0, the elastic constant (K33) was 13.9, and the rotational viscosity ($\gamma$1) was 60 millipascal seconds (mPas).

EXAMPLE 1

An exemplary embodiment of a liquid crystal composition (Example 1) is shown below in Table 3.

TABLE 3

| Liquid crystal compound | Content (wt %) |
|---|---|
| Chemical Formula A-1 | 23 |
| Chemical Formula A-3 | 8 |
| Chemical Formula A-6 | 6.5 |
| Chemical Formula 1-1 | 15 |
| Chemical Formula P-1 | 10 |
| Chemical Formula P-3 | 15 |
| Chemical Formula P-10 | 5.5 |
| Chemical Formula P-12 | 17 |

In Table 3 above, the liquid crystal composition of Example 1 includes liquid crystal molecules having a structure of Chemical Formula 1, i.e. a compound including a difluorine group, and having a negative dielectric anisotropy among the liquid crystal molecules. Specifically, Example 1 includes liquid crystal molecules having a structure represented by Chemical Formula 1-1.

The physical properties of Example 1 were as follows: the nematic-isotropic phase transition temperature (Tni) was 78 degrees Celsius, the refractive index ($\Delta$n) was 0.108, the dielectric anisotropy ($\Delta\epsilon$) was 4.88, the elastic constant (K33) was 12.0, and the rotational viscosity ($\gamma$1) was 85 mPas.

EXAMPLE 2

Another exemplary embodiment of a liquid crystal composition (Example 2) is shown below in Table 4.

TABLE 4

| liquid crystal compound | Content (wt %) |
|---|---|
| Chemical Formula A-1 | 37.5 |
| Chemical Formula A-3 | 1 |
| Chemical Formula A-6 | 6 |
| Chemical Formula 1-2 | 15 |
| Chemical Formula P-1 | 4.5 |
| Chemical Formula P-3 | 15 |
| Chemical Formula P-9 | 7.5 |
| Chemical Formula P-10 | 5.5 |
| Chemical Formula P-12 | 8.5 |

In Table 4 above, the liquid crystal composition of Example 2 includes liquid crystal molecules having a structure of Chemical Formula 1, i.e. a compound having a difluorine group and having a negative dielectric anisotropy. Specifically, the composition of Example 2 includes liquid crystal molecules having a structure represented by Chemical Formula 1-2.

The physical properties of Example 2 were as follows: the nematic-isotropic phase transition temperature (Tni) was 78 degrees Celsius, the refractive index ($\Delta n$) was 0.108, the dielectric anisotropy ($\Delta \epsilon$) was 4.9, the elastic constant (K33) was 14.1, and the rotational viscosity ($\gamma 1$) was 84 mPas.

EXAMPLE 3

Another exemplary embodiment of a liquid crystal composition (Example 3) is shown below in Table 5.

TABLE 5

| liquid crystal compound | Content (wt %) |
|---|---|
| Chemical Formula A-1 | 26 |
| Chemical Formula A-3 | 5 |
| Chemical Formula A-6 | 6.5 |
| Chemical Formula 2-1 | 15 |
| Chemical Formula P-1 | 10 |
| Chemical Formula P-3 | 15 |
| Chemical Formula P-5 | 3.5 |
| Chemical Formula P-10 | 4 |
| Chemical Formula P-12 | 15 |

In Table 5 above, the liquid crystal composition of Example 3 includes liquid crystal molecules having a structure of Chemical Formula 2, i.e. a compound having biphenyl group with a methyl group at a meta-position on one of the phenyl rings, and having a negative dielectric anisotropy. Specifically, the composition of Example 3 includes liquid crystal molecules having a structure represented by Chemical Formula 2-1.

The physical properties of Example 3 were as follows: the nematic-isotropic phase transition temperature (Tni) was 78 degrees Celsius, the refractive index ($\Delta n$) was 0.109, the dielectric anisotropy ($\Delta \epsilon$) was 4.79, the elastic constant (K33) was 11.9, and the rotational viscosity ($\gamma 1$) was 84 mPas.

EXAMPLE 4

Example 4 is identical to the content of the liquid crystal composition in Example 3 but includes 15 wt % of the liquid crystal molecules represented by Chemical Formula 2-2 instead of the liquid crystal molecule represented by Chemical Formula 2-1.

The physical properties of Example 4 were as follows: the nematic-isotropic phase transition temperature (Tni) was 70 degrees Celsius, the refractive index ($\Delta n$) was 0.108, dielectric anisotropy ($\Delta \epsilon$) was 5.0, the elastic constant (K33) was 13.5, and the rotation viscosity ($\gamma 1$) was 79 mPas.

EXAMPLE 5

Another exemplary embodiment of a liquid crystal composition (Example 5) is shown below in Table 6.

TABLE 6

| liquid crystal compound | Content (%) |
|---|---|
| Chemical Formula A-1 | 40 |
| Chemical Formula A-6 | 5.5 |
| Chemical Formula 3-1 | 15 |
| Chemical Formula P-1 | 10 |
| Chemical Formula P-3 | 15 |
| Chemical Formula P-9 | 8 |
| Chemical Formula P-10 | 6.5 |

In Table 6 above, the liquid crystal composition of Example 5 includes liquid crystal molecules having a structure of Chemical Formula 3, i.e. a 1,3-dioxane compound having a negative dielectric anisotropy. Specifically, composition of Example 5 includes liquid crystal molecules having a structure represented by Chemical Formula 3-1.

The physical properties of Example 5 were as follows: the nematic-isotropic phase transition temperature (Tni) was 78.5 degrees Celsius, the refractive index ($\Delta n$) was 0.108, the dielectric anisotropy ($\Delta \epsilon$) was 5.2, the elastic constant (K33) was 12.4, and the rotation viscosity ($\gamma 1$) was 82 mPas.

EXAMPLE 6

Example 6 is identical to the content of other liquid crystal molecule in Example 5, but includes 15 wt % of the liquid crystal molecule represented by Chemical Formula 3-2 instead of the liquid crystal molecule represented by Chemical Formula 3-1.

The physical properties of Example 6 were as follows: the nematic-isotropic phase transition temperature (Tni) was 78 degrees Celsius, the refractive index ($\Delta n$) was 0.110, the dielectric anisotropy ($\Delta \epsilon$) was 4.92, the elastic constant (K33) was 14.2, and the rotation viscosity ($\gamma 1$) was 78 mPas.

The Comparative Example including only the liquid crystal molecules having a positive dielectric anisotropy, and Examples 1 to 6 including the liquid crystal molecules having a negative dielectric anisotropy represented by Chemical Formulas 1-1 and 1-2, Chemical Formulas 2-1 and 2-2, and Chemical Formulas 3-1 and 3-2, show a difference in the light transmittance, but no significant difference in the physical properties. Specifically, in the examples of the liquid crystal composition including 15 wt % of liquid crystal molecules having a negative dielectric anisotropy, the transmittance was increased by about 5% as compared to the Comparative Example. More specifically, the transmittance increasing effects are described with reference to Table 7 below.

TABLE 7

| | | Comparative Example | Example 2 |
|---|---|---|---|
| Light Characteristic | Maximum voltage ($V_{max}$) | 5.1 V | 5.2 V |
| | transmittance | 100.0% | 105.2% |

The above Table 7 shows the Light Characteristic results of Example 2 including the liquid crystal molecule represented by Chemical Formula 1-2 in an amount of 15 wt %, and the Comparative Example including only liquid crystal molecules having a positive dielectric anisotropy. Referring to Table 7, in the case of Example 2, the transmittance is increased by about 5.2% at the same maximum voltage as compared to the Comparative Example. This effect may also be seen in FIG. 4 and FIG. 5.

Figure 4:
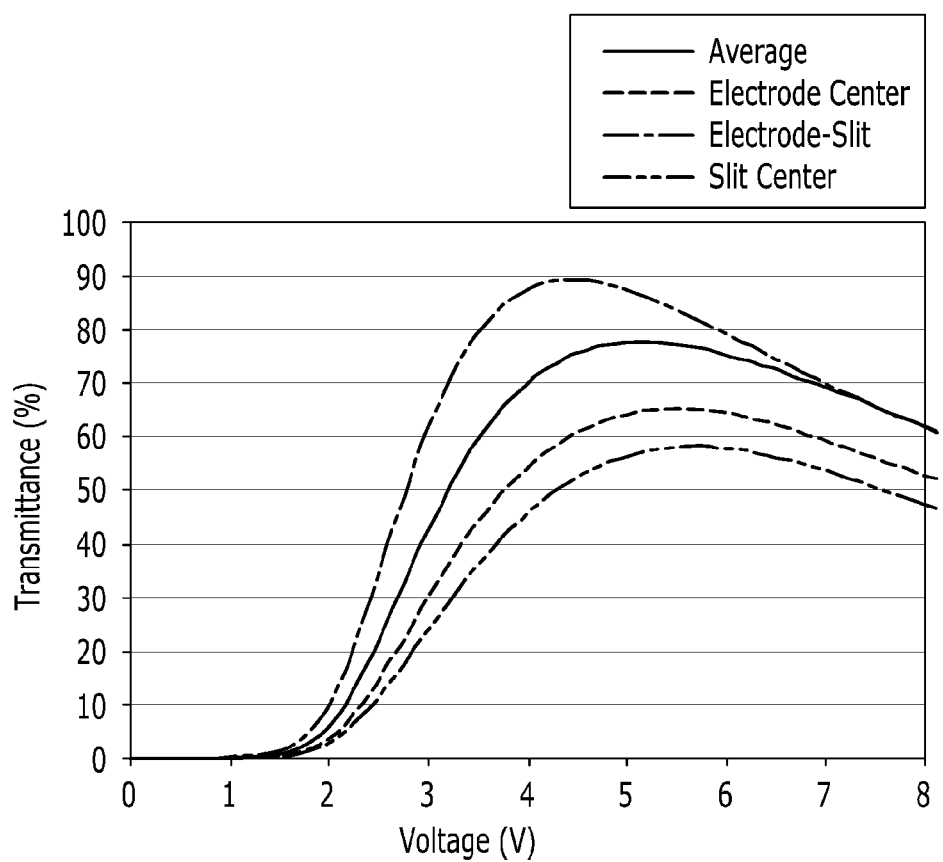
FIG. 4 is a graph illustrating the percent transmittance (%) versus the voltage (V) of a liquid crystal display in accordance with a comparative example.
Figure 5:
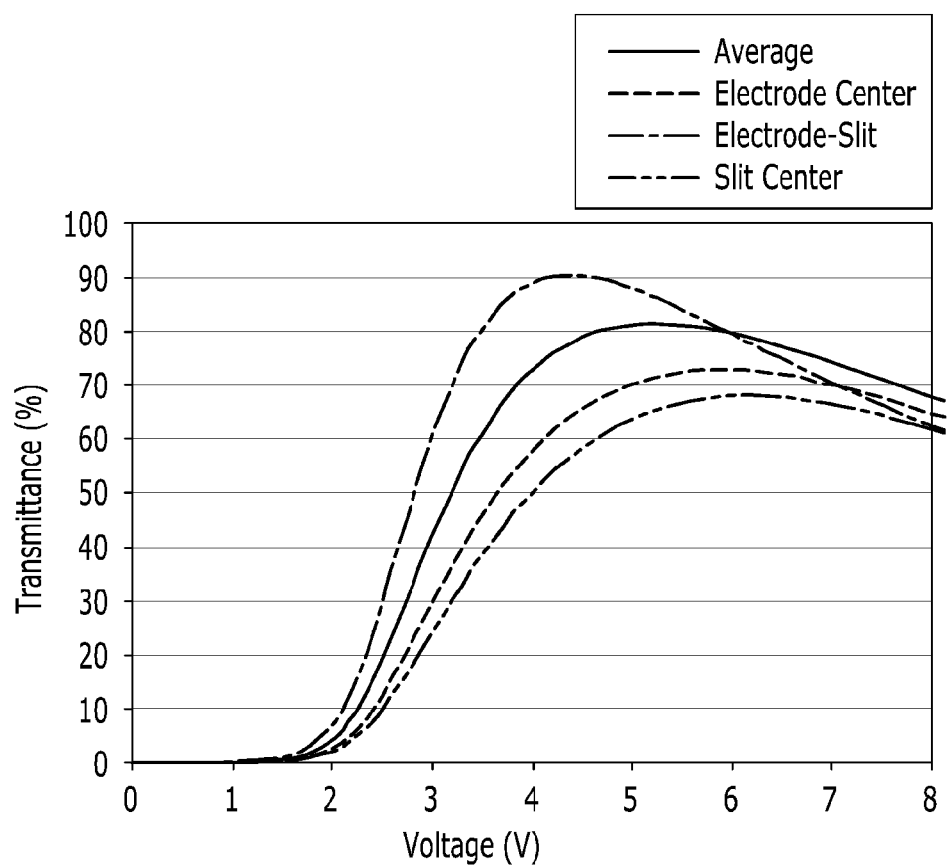
FIG. 5 is a graph illustrating the percent transmittance (%) versus the voltage (V) of a liquid crystal display in accordance with an Example embodiment.

FIG. 4 is graph illustrating the transmittance versus the voltage of a liquid crystal display including the liquid crystal composition of Comparative Example, and FIG. 5 is graph illustrating the transmittance versus the voltage of a liquid crystal display including the liquid crystal composition of Example 2.

FIG. 4 and FIG. 5 show the transmittance in the electrode center region, the electrode edge region, the slit center region and the average transmittance of the liquid crystal display.

Referring to FIG. 4 and FIG. 5, the light transmittance in the electrode center region, the electrode-slit region and the slit center region is increased as compared to the Comparative Example. Specifically, the light transmittance of the electrode center region is increased from about 65% to about 72%, and the light transmittance of the slit center region is increased from about 59% to about 69%. Thus, the light transmittance shows significant increasing effects.

As described and shown above, without being limited by theory, it is believed that when the liquid crystal compositions including liquid crystal molecules represented by Chemical Formulas 1 to 3 having a negative dielectric anisotropy are used, the transmittance is increased due to a decrease in a splay angle of the liquid crystal between the electrodes.

Specifically, the transmittance is increased due to a decrease in the rotation of the liquid crystals at the edge periphery portion of an electrode having the strongest horizontal field.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A liquid crystal composition comprising:
   at least one liquid crystal molecule selected from liquid crystal molecules represented by Chemical Formulas 1 to 3 below:

Chemical Formula 1

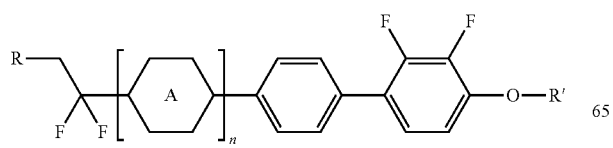

Chemical Formula 2

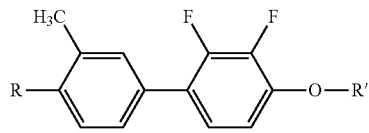

Chemical Formula 3

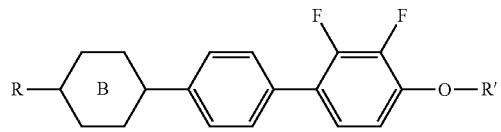

wherein,
in Chemical Formulas 2 and 3 above, R and R' are each independently a hydrogen, a C1 to C5 alkyl group, a halogen group, or —CN;
in Chemical Formula 1 above, n is an integer from 0 to 3, R is a hydrogen, R' is a hydrogen, a C1 to C5 alkyl group, a halogen group, or —CN, and A is of the following formulas

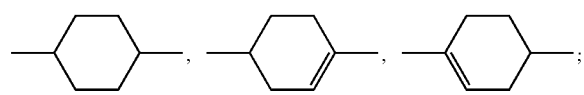

and
in Chemical Formula 3 above, B is of the following formulas

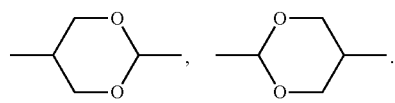

2. The liquid crystal composition of claim 1, wherein the liquid crystal molecules represented by Chemical Formulas 1 to 3 comprise liquid crystal molecules represented by Chemical Formula 1-1, Chemical Formula 1-2, Chemical Formula 2-1, Chemical Formula 2-2, and Chemical Formula 3-1 below:

Chemical Formula 1-1

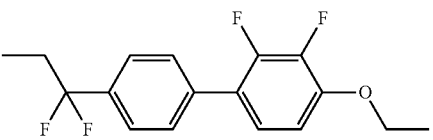

Chemical Formula 1-2

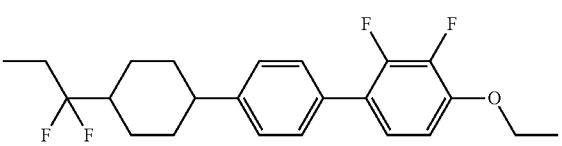

Chemical Formula 2-1

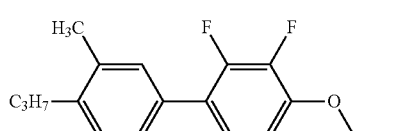

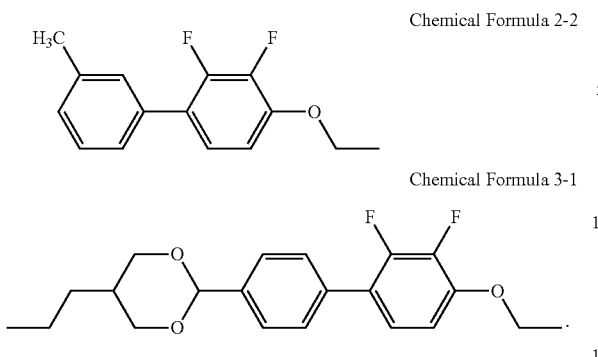

3. The liquid crystal composition of claim 2,
further comprising at least one alkenyl-based liquid crystal molecule selected from Chemical Formulas A-1 to A-7 below:

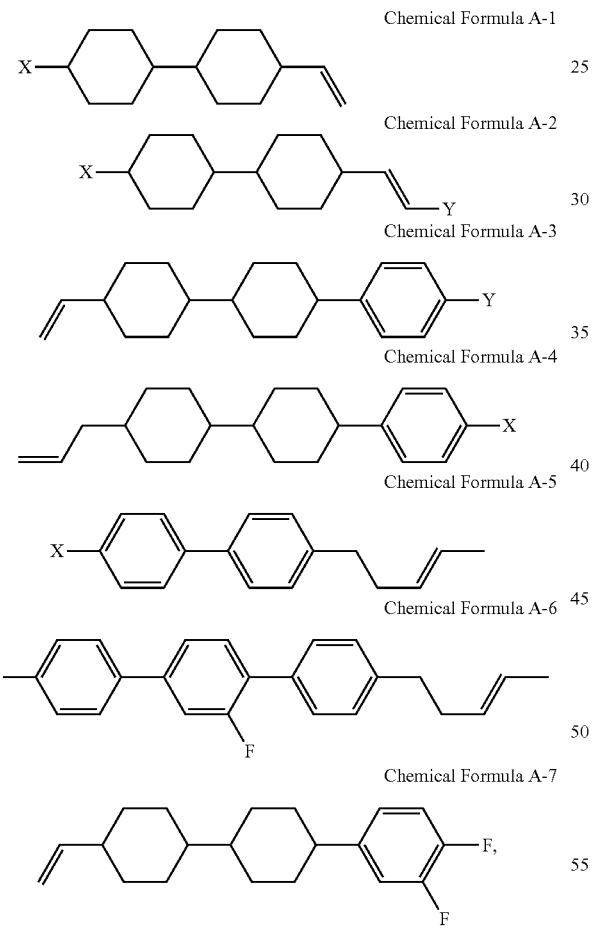

wherein,
in Chemical Formulas A-1 to A-7 above, X and Y are each independently a C1 to C5alkyl group.

4. The liquid crystal composition of claim 3,
further comprising at least one neutral liquid crystal molecule selected from Chemical Formulas N-1 to N-7 below:

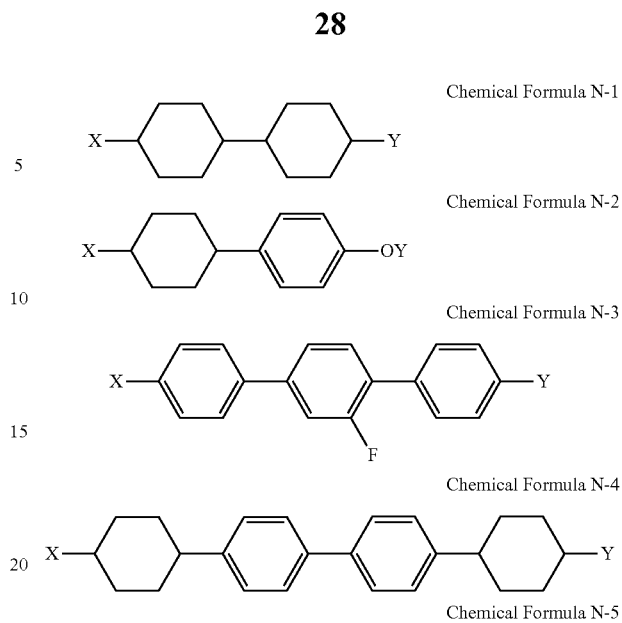

wherein,
in Chemical Formulas N-1 to N-5 above, X and Y are each independently a C1 to C5alkyl group.

5. The liquid crystal composition of claim 4,
further comprising at least one polar liquid crystal molecule selected from Chemical Formulas P-1 to P-12 below:

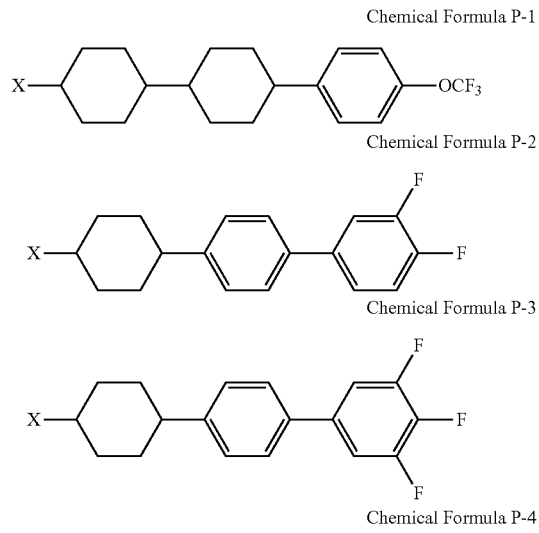

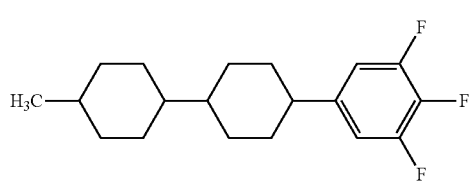

-continued

Chemical Formula P-5
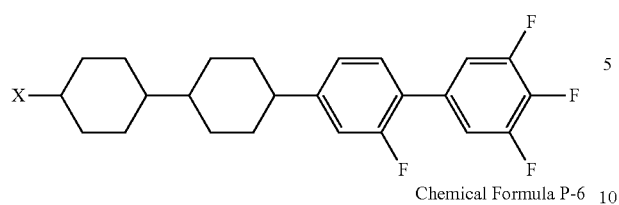

Chemical Formula P-6
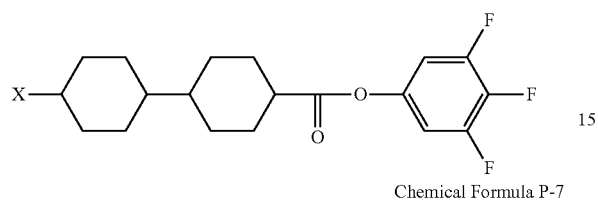

Chemical Formula P-7
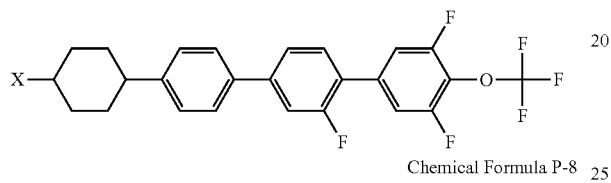

Chemical Formula P-8
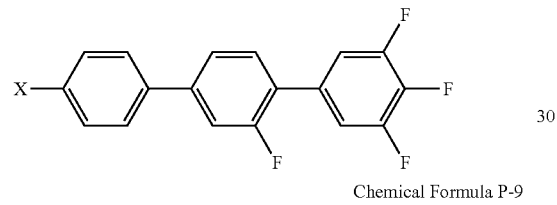

Chemical Formula P-9
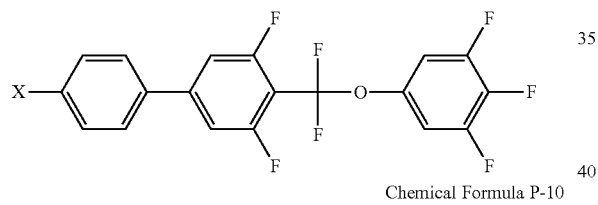

Chemical Formula P-10
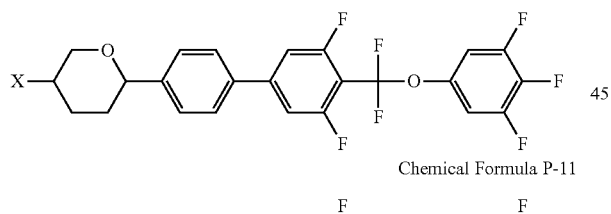

Chemical Formula P-11
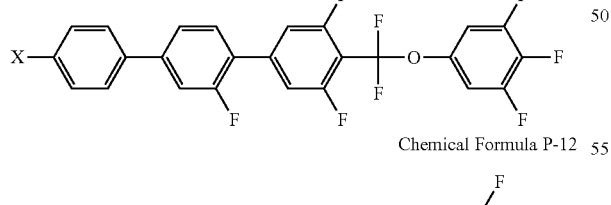

Chemical Formula P-12
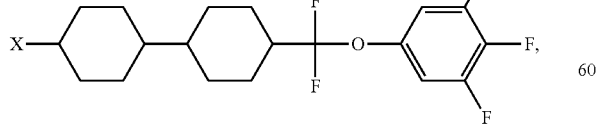

wherein,
in Chemical Formulas P-1 to P-12 above, X and Y are each independently a C1 to C5 alkyl group.

6. The liquid crystal composition of claim 5, comprising about 1 wt% to about 20 wt% of at least one of the liquid crystal molecules selected from Chemical Formula 1-1, Chemical Formula 1-2, Chemical Formula 2-1, Chemical Formula 2-2, Chemical Formula 3-1, and Chemical Formula 3-2, based on the entire weight of the composition.

7. A liquid crystal display comprising:
a first substrate,
a first electrode and a second electrode positioned on the first substrate,
an insulating layer interposed between the first electrode and the second electrode,
a second substrate facing the first substrate; and
a liquid crystal layer positioned between the first substrate and the second substrate,
wherein the liquid crystal layer comprises at least one liquid crystal molecule selected from liquid crystal molecules represented by Chemical Formulas 1 to 3 below:

Chemical Formula 1
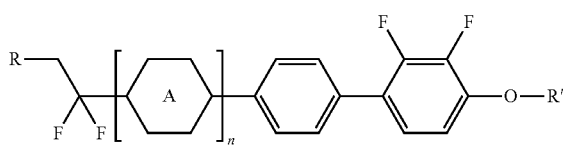

Chemical Formula 2
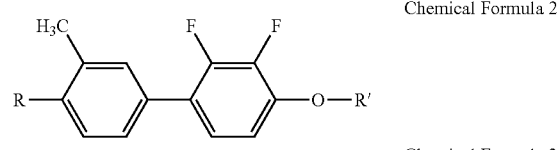

Chemical Formula 3
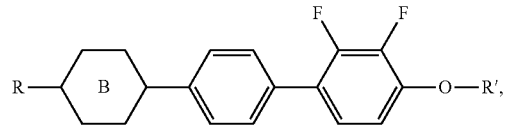

wherein
in Chemical Formulas 2 and 3 above, R and R' are each independently a hydrogen, a C1 to C5 alkyl group, a halogen group, or —CN;
in Chemical Formula 1 above, n is an integer from 0 to 3, R is a hydrogen, R' is independently a hydrogen, a C1 to C5 alkyl group, a halogen group, or —CN, and A is of the following formulas

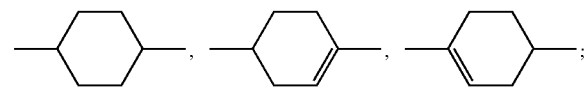

and
in Chemical Formula 3 above, B is of the following formulas

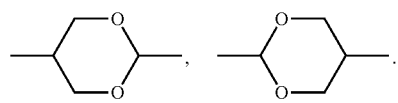

8. The liquid crystal display of claim 7, wherein
the liquid crystal molecule represented by Chemical Formulas 1 to 3 comprise liquid crystal molecules represented by Chemical Formula 1-1, Chemical Formula 1-2, Chemical Formula 2-1, Chemical Formula 2-2, and Chemical Formula 3-1 below:

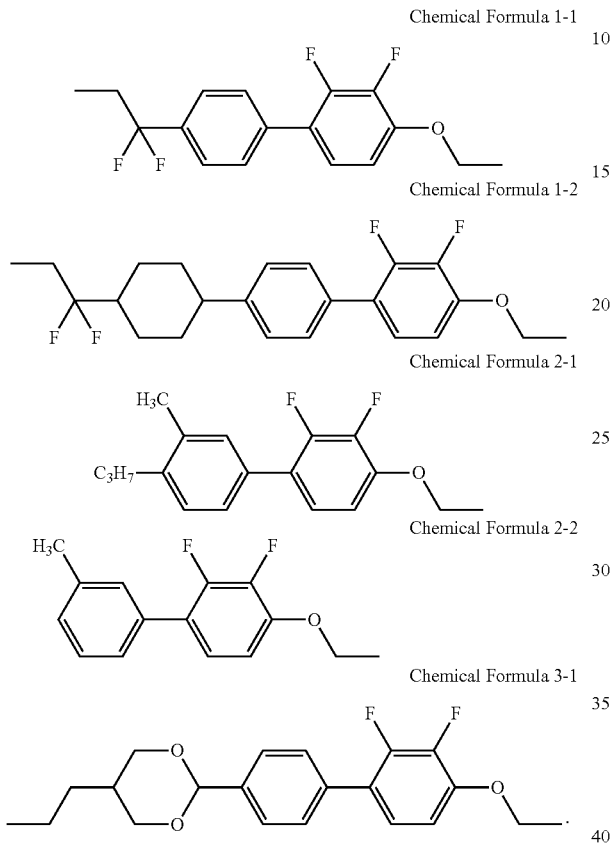

9. The liquid crystal display of claim 8,
further comprising at least one alkenyl-based liquid crystal molecule selected from Chemical Formulas A-1 to A-7 below:

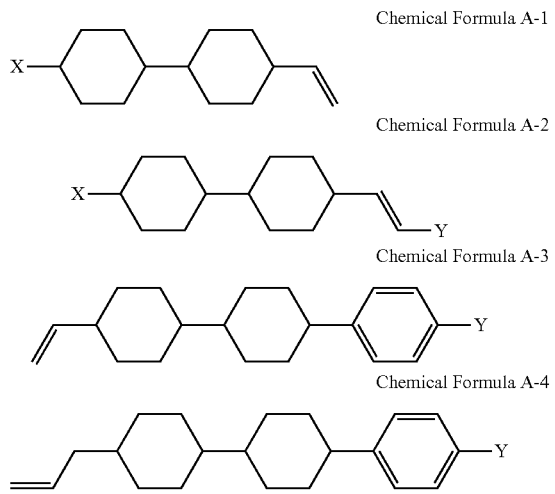

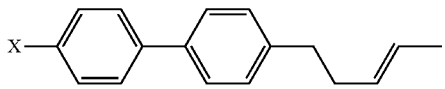

Chemical Formula A-5

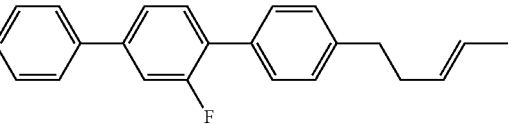

Chemical Formula A-6

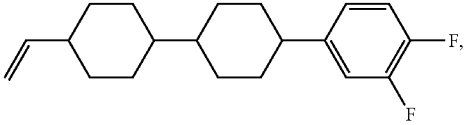

Chemical Formula A-7 wherein,
in Chemical Formulas A-1 to A-7 above, X and Y are each independently a C1 to C5 alkyl group.

10. The liquid crystal display of claim 9,
further comprising at least one neutral liquid crystal molecule selected from Chemical Formulas N-1 to N-7 below:

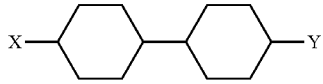

Chemical Formula N-1

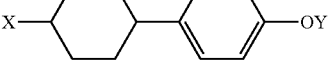

Chemical Formula N-2

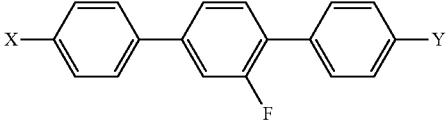

Chemical Formula N-3

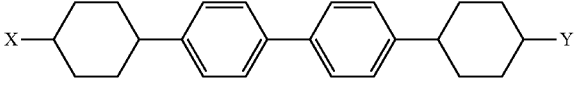

Chemical Formula N-4

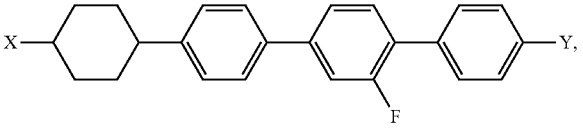

Chemical Formula N-5 wherein,
in Chemical Formulas N-1 to N-5 above, X and Y are each independently a C1 to C5 alkyl group.

11. The liquid crystal display of claim 10,
further comprising at least one polar liquid crystal molecule selected from Chemical Formulas P-1 to P-12 below:

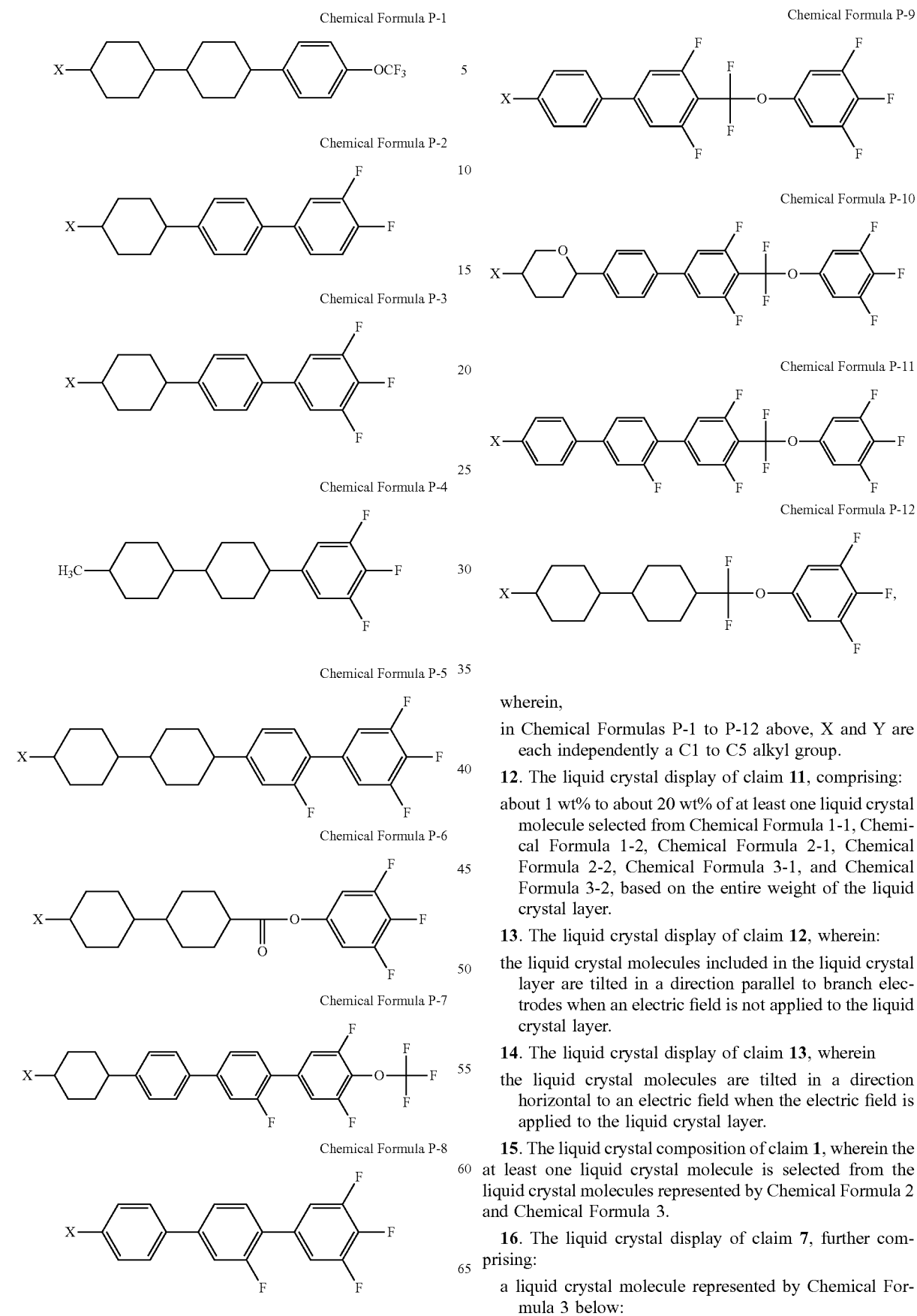

wherein,
in Chemical Formulas P-1 to P-12 above, X and Y are each independently a C1 to C5 alkyl group.

12. The liquid crystal display of claim 11, comprising:
about 1 wt% to about 20 wt% of at least one liquid crystal molecule selected from Chemical Formula 1-1, Chemical Formula 1-2, Chemical Formula 2-1, Chemical Formula 2-2, Chemical Formula 3-1, and Chemical Formula 3-2, based on the entire weight of the liquid crystal layer.

13. The liquid crystal display of claim 12, wherein:
the liquid crystal molecules included in the liquid crystal layer are tilted in a direction parallel to branch electrodes when an electric field is not applied to the liquid crystal layer.

14. The liquid crystal display of claim 13, wherein
the liquid crystal molecules are tilted in a direction horizontal to an electric field when the electric field is applied to the liquid crystal layer.

15. The liquid crystal composition of claim 1, wherein the at least one liquid crystal molecule is selected from the liquid crystal molecules represented by Chemical Formula 2 and Chemical Formula 3.

16. The liquid crystal display of claim 7, further comprising:
a liquid crystal molecule represented by Chemical Formula 3 below:

Chemical Formula 3
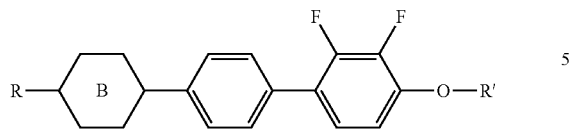
wherein, B is of the following formulas
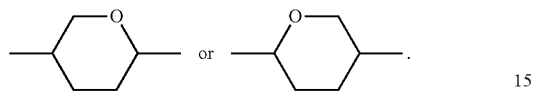
17. The liquid crystal display of claim 16, wherein the liquid crystal molecules represented by Chemical Formula 3 comprise liquid crystal molecules represented by Chemical Formula 3-2, below:
Chemical Formula 3-2
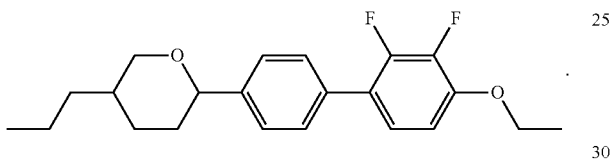
* * * * *